(12) United States Patent
Han et al.

(10) Patent No.: US 9,156,764 B2
(45) Date of Patent: Oct. 13, 2015

(54) PROCESS FOR MAKING ETHYLENE AND ACETIC ACID

(71) Applicant: Rohm and Haas Company, Philadelphia, PA (US)

(72) Inventors: Scott Han, Lawrenceville, NJ (US); Christopher D. Frick, Pottstown, PA (US); Daniel J. Martenak, Perkasie, PA (US)

(73) Assignee: Rohm and Haas Company

( * ) Notice: Subject to any disclaimer, the term of this patent is extended or adjusted under 35 U.S.C. 154(b) by 0 days.

(21) Appl. No.: 14/387,687

(22) PCT Filed: Feb. 12, 2013

(86) PCT No.: PCT/US2013/025728
§ 371 (c)(1),
(2) Date: Sep. 24, 2014

(87) PCT Pub. No.: WO2013/148006
PCT Pub. Date: Oct. 3, 2013

(65) Prior Publication Data
US 2015/0045582 A1 Feb. 12, 2015

Related U.S. Application Data

(60) Provisional application No. 61/616,572, filed on Mar. 28, 2012.

(51) Int. Cl.
| | | |
|---|---|---|
| *B01J 23/648* | (2006.01) | |
| *C07C 5/333* | (2006.01) | |
| *C07C 51/215* | (2006.01) | |
| *C07C 5/48* | (2006.01) | |
| *B01J 23/00* | (2006.01) | |
| *B01J 23/652* | (2006.01) | |
| *B01J 27/057* | (2006.01) | |
| *B01J 37/02* | (2006.01) | |
| *B01J 37/08* | (2006.01) | |
| *B01J 35/02* | (2006.01) | |
| *B01J 37/00* | (2006.01) | |

(52) U.S. Cl.
CPC ............ *C07C 51/215* (2013.01); *B01J 23/002* (2013.01); *B01J 23/6525* (2013.01); *B01J 27/0576* (2013.01); *B01J 35/023* (2013.01); *B01J 37/0036* (2013.01); *B01J 37/0236* (2013.01); *B01J 37/08* (2013.01); *C07C 5/3332* (2013.01); *C07C 5/3337* (2013.01); *C07C 5/48* (2013.01); *B01J 2523/00* (2013.01); *C07C 2523/20* (2013.01); *C07C 2523/22* (2013.01); *C07C 2523/28* (2013.01); *C07C 2523/44* (2013.01); *C07C 2523/652* (2013.01); *C07C 2527/057* (2013.01)

(58) Field of Classification Search
None
See application file for complete search history.

(56) References Cited

U.S. PATENT DOCUMENTS

| | | | | |
|---|---|---|---|---|
| 5,162,578 A | * | 11/1992 | McCain et al. | ............ 562/512.2 |
| 5,907,056 A | * | 5/1999 | Karim et al. | .................. 562/549 |
| 6,030,920 A | † | 2/2000 | Karim | |
| 7,718,568 B2 | † | 5/2010 | Gaffney | |
| 8,642,825 B2 | † | 2/2014 | Kustov | |
| 2008/0132723 A1 | * | 6/2008 | Johnston et al. | .............. 560/241 |
| 2010/0256432 A1 | * | 10/2010 | Arnold et al. | ................. 585/655 |
| 2011/0245571 A1 | * | 10/2011 | Kustov et al. | ................. 585/658 |

* cited by examiner
† cited by third party

*Primary Examiner* — Yevegeny Valenrod

(57) ABSTRACT

A process comprising catalytically converting ethane to ethylene and acetic acid in the presence of oxygen at a temperature of 450° C. or less in the gas phase wherein the catalyst has the empirical formula $MoV_aNb_bTe_cZ_dO_n$.

10 Claims, No Drawings

PROCESS FOR MAKING ETHYLENE AND ACETIC ACID

CROSS-REFERENCE TO RELATED APPLICATIONS

This application claims priority from provisional application Ser. No. 61/616,572, filed Mar. 28, 2012, which is incorporated herein by reference in its entirety.

BACKGROUND OF THE INVENTION

The invention relates to a process for low temperature dehydrogenation of ethane to ethylene and acetic acid in the presence of oxygen, and particularly to a process using a catalyst featuring good conversion and good selectivity.

Low temperature oxydehydrogenation of ethane to ethylene has become well known since the publication of "The Oxidative Dehydrogenation of Ethane over Catalyst Containing Mixed Oxide of Molybdenum and Vanadium" by E. M. Thorsteinson, T. P. Wilson, F. G. Young and P. H. Kasai, Journal of Catalysis 52, pp. 116-132 (1978). This article discloses mixed oxide catalysts containing molybdenum and vanadium together with another transition metal oxide (Ti, Cr, Mn, Fe, Co, Ni, Nb, Ta, or Ce). The catalysts are active at temperatures as low as 200° C. for the oxydehydrogenation of ethane to ethylene.

The effectiveness of the oxydehydrogenation of ethane to ethylene is usually primarily determined by two parameters: conversion of ethane, and selectivity (efficiency) to ethylene. As used herein, these terms are defined as follows:

$$\text{conversion of ethane} = \frac{[CO]/2 + [CO_2]/2 + [C_2H_4]}{[CO]/2 + [CO_2]/2 + [C_2H_4] + [C_2H_6]}$$

$$\text{selectivity (efficiency) to ethylene} = \frac{[C_2H_4]}{[CO]/2 + [CO_2]/2 + [C_2H_4]}$$

wherein: [ ]=relative moles of the component and the production of acetic acid is negligible. The terms in the art are sometimes calculated differently but the values calculated either way are substantially the same.

Under certain reaction conditions, substantial amounts of acetic acid can be formed as a co-product and the effectiveness of the reaction to ethylene and acetic acid is calculated by the following equations:

$$\text{conversion of ethane} =$$
$$\frac{[CO]/2 + [CO_2]/2 + [C_2H_4] + [CH_3COOH]}{[CO]/2 + [CO_2]/2 + [C_2H_4] + [C_2H_6] + [CH_3COOH]}$$

$$\text{selectivity (efficiency) to ethylene and acetic acid} =$$
$$\frac{[C_2H_4] + [CH_3COOH]}{[CO]/2 + [CO_2]/2 + [C_2H_4] + [C_2H_6] + [CH_3COOH]}$$

One application of a catalytic ethane to ethylene and acetic acid process would be as a front end process for commercial vinyl acetate monomer (VAM) synthesis. The reaction of acetic acid with ethylene (acetoxylation) is the dominant route to vinyl acetate today. Because current vinyl acetate process technology is mature, accomplishing significant improvements has become increasingly difficult. A reduction in feedstock costs would lead to cost-savings in the production of VAM. The use of ethane and oxygen as starting feedstock would represent a significant savings in raw material cost over the currently-used ethylene and acetic acid.

It would be desirable to have a process which reacts ethane with oxygen over a catalyst to selectively coproduce a product stream comprising ethylene and acetic acid, which product stream could be used in VAM production.

SUMMARY OF THE INVENTION

The disclosed process is such a process comprising catalytically converting ethane to ethylene and acetic acid in the presence of oxygen at a temperature of 450° C. or less in the gas phase wherein the catalyst has the empirical formula $MoV_aNb_bTe_cZ_dO_n$ wherein Z is at least one element selected from the group consisting of W, Cr, Ta, Ti, Zr, Hf, Mn, Re, Fe, Ru, Co, Rh, Ni, Pd, Pt, Ag, Au, Zn, B, Al, Ga, In, Ge, Sn, Pb, P, Bi, Y, rare earth elements and alkaline earth elements, a=0.01 to less than 1.0, b=0.01 to less than 1.0, c=0.01 to less than 1.0, d=0.0 to less than 1.0 and n is determined by the oxidation states of the other elements.

Surprisingly, the process can be operated at very high selectivity to ethylene.

DETAILED DESCRIPTION OF THE INVENTION

The process of the invention converts ethane to ethylene and acetic acid in the presence of oxygen and a catalyst.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers. Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth)acrylic acid" refers to either acrylic acid or methacrylic acid.

The raw material used as the source of the ethane advantageously is a gas stream which contains at least three volume percent of ethane. The ethane-containing gas stream is not limited and can be, for example, derived from natural gas or from a by-product stream from a chemical or petroleum process. The ethane-containing gas stream can contain minor amounts of hydrogen, carbon monoxide, and $C_3$-$C_4$ alkanes and alkenes, e.g. less than five volume percent of each. The ethane-containing gas stream can also contain major amounts, e.g., more than five volume percent each, of one or more of nitrogen, methane, carbon dioxide, and water in the form of steam.

An oxygen-containing gas provides molecular oxygen to the reaction system. The term "oxygen-containing gas," as used herein, refers to any gas comprising from 0.01% up to 100% oxygen, including, for example, air. While the oxygen-containing gas may be pure oxygen gas, it is usually more economical and practical to use an oxygen-containing gas such as air.

A diluting gas may be employed for the purpose of diluting the reactant gases. Suitable diluting gases include, but are not limited to, one or more of: carbon monoxide, carbon dioxide, nitrogen, argon, helium, and mixtures thereof. A suitable molar ratio of the starting materials for the initial feed gas (hydrocarbon):(oxygen):(diluting gas):($H_2O$), would be, for example, (1):(0.1 to 10):(0 to 20):(0.2 to 70), for example, including but not limited to, (1):(1 to 5.0):(0 to 10):(5 to 40). The diluting gas may be employed to adjust the space velocity, the oxygen partial pressure and the steam partial pressure.

As used herein, "mixed metal oxide catalyst" refers to a catalyst comprising more than one metal oxide.

According to one embodiment of the invention, suitable catalysts in accordance with the invention are one or more mixed metal oxide catalysts having the empirical formula $MoV_aNb_bTe_cZ_dO_n$ wherein Z is at least one element selected from the group consisting of W, Cr, Ta, Ti, Zr, Hf, Mn, Re, Fe, Ru, Co, Rh, Ni, Pd, Pt, Ag, Au, Zn, B, Al, Ga, In, Ge, Sn, Pb, P, Bi, Y, rare earth elements and alkaline earth elements, a=0.01 to less than 1.0, b=0.01 to less than 1.0, c=0.01 to less than 1.0, d=0.0 to less than 1.0 and n is determined by the oxidation states of the other elements. In one embodiment of the invention, Z is Pd. Preparation of the mixed metal oxide (MMO) catalysts is described in U.S. Pat. No. 7,304,014. A precursor slurry of mixed metal salts is first prepared by conventional methods and methods described in U.S. Pat. No. 7,304,014 that include, but are not limited to for example, rotary evaporation, drying under reduced pressure, hydrothermal methods, co-precipitation, solid-state synthesis, impregnation, incipient wetness, sol gel processing and combinations thereof. After the precursor slurry is prepared, it is dried according to conventional drying methods including, but not limited to for example, drying in ovens, spray drying and freeze drying. The dried precursor is then calcined to obtain prepared MMO catalysts using well known techniques and techniques described above to those having skill in the art including, but not limited to, for example, flow calcinations, static calcinations, rotary calcinations and fluid-bed calcinations. In some cases the prepared MMO catalysts are further milled to improve their catalytic activity.

The modified mixed metal oxide (promoted or not) may be used by itself as a solid catalyst. The catalyst also may be combined with one or more suitable carriers, such as, without limitation, silica, alumina, titania, aluminosilicate, diatomaceous earth or zirconia, according to art-disclosed techniques. Further, it may be processed to a suitable shape or particle size using art disclosed techniques, depending upon the scale or system of the reactor.

Alternatively, the metal components of the catalyst are supported on materials such as alumina, silica, silica-alumina, zirconia, titania, etc. by conventional incipient wetness techniques. In one method, solutions containing the metals are contacted with the dry support such that the support is wetted, then the resultant wetted material is dried, for example, at a temperature from room temperature to 200° C., followed by calcination as described above. In another method, solutions of metal ions are contacted with the support, typically in volume ratios of greater than 3:1 (metal ion solution:support), and the solution is agitated such that the metal ions are ion-exchanged onto the support. The metal-containing support is then dried and calcined as detailed above.

According to a separate embodiment, catalysts are also prepared using one or more promoters. The starting materials for the above promoted mixed metal oxide are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

In addition, with reference to the promoter elements for the promoted catalyst, the nickel source may include nickel(II) acetate tetrahydrate, $Ni(NO_3)_2$, nickel(II) oxalate, NiO, $Ni(OH)_2$, $NiCl_2$, $NiBr_2$, nickel(II) acetylacetonate, nickel(II) sulfate, NiS or nickel metal. The palladium source may include $Pd(NO_3)_2$, palladium(II) acetate, palladium oxalate, PdO, $Pd(OH)_2$, $PdCl_2$, palladium acetylacetonate or palladium metal. The silver source may be silver acetate, silver acetylacetonate, silver benzoate, silver bromide, silver carbonate, silver chloride, silver citrate hydrate, silver fluoride, silver iodide, silver lactate, silver nitrate, silver nitrite, silver oxide, silver phosphate or a solution of silver in an aqueous inorganic acid, e.g., nitric acid. The gold source may be ammonium tetrachloroaurate, gold bromide, gold chloride, gold cyanide, gold hydroxide, gold iodide, gold oxide, gold trichloride acid and gold sulfide.

The reaction is advantageously carried out in conventional reactors with the ethane catalytically converted at conventional residence times such as, for example, times of greater than 100 milliseconds. Advantageously, the reactor system comprises one or more fixed and/or fluidized bed reactors. In one embodiment of the invention, the system comprises more than one reactor and one of the reactors is in catalyst regeneration mode.

The composition of the feed gas to the reactor may be varied according to parameters known to those skilled in the art. The reaction mixture employed in carrying out the process is generally one mol of ethane, 0.01 to 1.0 mol of molecular oxygen either as pure oxygen or in the form of air, and zero to 4.0 mol of water in the form of steam. The water or steam is used as a reaction diluent and as a heat moderator for the reaction. Other gases may be used as reaction diluent or heat moderators such as nitrogen, helium, carbon dioxide, and methane.

During the course of the reaction, one mole of water is formed for each mol of ethane that is converted. The water from the reaction results in the formation of some acetic acid. Under several atmospheres of pressure, about 1 to 50 mol of ethylene per mol of acetic acid is formed.

The gaseous components of the reaction mixture include ethane and oxygen, and possibly a diluent, and these components are uniformly admixed prior to being introduced into the reaction zone. The components may be preheated, individually or after being admixed, prior to being introduced into the reaction zone, which advantageously has a temperature of from about 200° C. to about 450° C.

The reaction zone generally has a pressure of from about 1 to 30 atmospheres absolute, preferably 1 to 20 atmospheres; a temperature of from about 150° C. to 450° C., preferably from about 200° C. to about 400° C.; a contact time between the reaction mixture and the catalyst of from about 0.1 to about 100 seconds, preferably from about 1 to 10 seconds; and a gas hourly space velocity of from about 50 to 500 $h^{-1}$, and preferably 200 to 300 $h^{-1}$.

The gas hourly space velocity is calculated by determining total reactor inlet gas volume in liters, expressed as the volume at 0° C. at 760 mm Hg, of the total feed over a period of one hour divided by the liters of catalyst in the reactor $$\text{space velocity} = \frac{\text{liters of inlet gas}}{\text{liters of catalyst in reactor}} = h^{-1}$$

The reaction pressure is initially provided by the feed of the gaseous reactant and diluent and, after the reaction has commenced, the pressure preferably is maintained by the use of suitable back-pressure controllers placed on the reactor outlet stream.

The reaction temperature is preferably provided by placing the catalyst bed within a tubular converter having walls immersed in a suitable heat transfer medium such as DOWTHERM brand thermal transfer fluid, available from The Dow Chemical Company, tetralin, molten salt mixtures, or other suitable heat transfer agents heated to the desired temperature.

Generally, the process can be carried out in a single stage with all of the oxygen for the reaction being supplied along with an inert diluent. The process can also be carried out in multiple stages. It is desirable to operate without a noncondensable diluent to facilitate the isolation of the ethylene produced.

A reasonably good basis for comparing catalyst performance can be obtained by comparing selectivity to ethylene for the same conversion of ethane. This can be accomplished easily by taking advantage of the relationship between selectivity to ethylene and conversion of ethane over the useable operating temperature range. Thus, it is unnecessary to actually operate at the conversion of ethane being used for a comparison because one can interpolate or extrapolate, according to mathematical methods known to those skilled in the art, to any desired set of values from two sets of data.

In one embodiment of the invention, the process is operated such that the selectivity to ethylene is greater than 80% at a greater than 10% conversion of ethane. In another embodiment, the process is operated such that the selectivity to ethylene is greater than 90% at a greater than 10% conversion of ethane. In one embodiment of the invention, for a conversion of ethane of at least 10%, the selectivity to ethylene is greater than 75% and the selectivity to acetic acid is greater than 15%. In one embodiment of the invention, the ratio of ethylene to acetic acid is less than 2 in the product stream.

High selectivity to desired products generally is highly advantageous. High ethylene selectivity would give significant processing advantages such as, for example:

1) High ethylene selectivity allows economical recycle of uncoverted ethane. Separation duties are reduced due to diminished production of COx gases and, in an extinction recycle process, all of the unreacted ethane is ultimately converted. Thus, the high ethylene selectivity is the yield obtained, as ethane conversion is ultimately 100%.
2) Higher grade ethylene product, if in excess, can be used for other chemical processes in a plant and it can be sold as a commodity feedstock chemical. Higher purity grades generally yield higher prices.
3) Frequently, for downstream vinyl acetate monomer processing needs, excess acetic acid is readily available. Thus, it is easy to make up the acetic acid volume to match ethylene yield. This would allow for increased VAM production rates and space-time yields.
4) High selectivity to ethylene and/or acetic acid reduces formation of COx gases. It is commonly known that formation of CO and $CO_2$ byproducts are the result of over-oxidation of the desired ethylene and acetic acid products. Such formation of COx gases consumes valuable feed carbon. High selectivity to the desired products reduces this waste production.

Specific Embodiments of the Invention

The following examples are given to illustrate the invention and should not be construed as limiting its scope.

EXAMPLES

Catalyst Preparation

The catalysts used in this study are prepared according to the procedures described in U.S. Pat. No. 7,304,014, assigned to Rohm and Haas Company.

Preparation 1—Unpromoted Mo/V/Te/Nb Mixed Metal Oxide Catalyst Preparation

A catalyst of nominal composition $Mo_{1.0}V_{0.3}Te_{0.23}Nb_{0.17}O_x$ is prepared in the presence of nitric acid and treated with methanol in the following manner. 200 mL of an aqueous solution containing ammonium heptamolybdate tetrahydrate (1.0M Mo), ammonium metavanadate (0.3M V) and telluric acid (0.23M Te), formed by dissolving the corresponding salts in water at 70° C., is added to a 2000 mL rotavap flask. Then, 200 mL of an aqueous solution of ammonium niobium oxalate (0.17M Nb), oxalic acid (0.155M) and nitric acid (0.24M) are added thereto. After removing the water via a rotary evaporator with a warm water bath at 50° C. and 28 mm Hg, the solid materials are further dried in a vacuum oven at 25° C. overnight and then calcined. Calcination is effected by placing the solid materials in an air atmosphere and then heating them to 275° C. at 10° C./min and holding them for one hour; the atmosphere is then changed to argon and the material is heated from 275° C. to 600° C. at 2° C./min and the material is held under the argon atmosphere at 600° C. for two hours. The catalyst, thus obtained, is ground with a Freezer/Mill (Model 6750 from Spex CertiPrep, Metuchen, N.J.), and is then extracted with methanol in a Soxhlet apparatus for 5 hours. The solids are dried in a vacuum oven and sieved to 14-20 mesh granules for reactor evaluation. The resulting catalyst is employed in Examples 1, 2, 4 and 5.

Preparation 2—Pd-promoted Mo/V/Te/Nb Mixed Metal Oxide Catalyst Preparation

A catalyst of nominal composition $Mo_{1.0}V_{0.3}Te_{0.23}Nb_{0.17}Pd_{0.041}O_x$ is prepared in the presence of nitric acid and treated with methanol in the following manner 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., is added to a 2000 mL rotavap flask. Then 200 mL of an aqueous solution of ammonium niobium oxalate (0.17M Nb), palladium nitrate hydrate (0.0M Pd), oxalic acid (0.155M) and nitric acid (0.24M) are added thereto. After removing the water via a rotary evaporator with a warm water bath at 50° C., and 28 mm Hg, the solid materials are further dried in a vacuum oven at 25° C. overnight and then calcined. (Calcination is effected by placing the solid materials in an air atmosphere and then heating them to 275° C. at 10° C./min and holding them for one hour; the atmosphere is then changed to argon and the material is heated from 275° C. to 600° C. at 2° C./min and the material is held under the argon atmosphere at 600° C. for two hours.) The catalyst thus obtained is ground with a Freezer/Mill (Model 6750 from Spex CertiPrep™), then extracted with methanol in a Soxhlet apparatus for 5 hours. The solids are dried in a vacuum oven and sieved to 14-20 mesh granules for reactor evaluation. The resulting promoted catalyst is employed in Examples 3 and 6.

Examples 1-6

Ethane is converted under the conditions described in Table 1. The catalyst used is as described in Preparations 1 and 2. The catalyst (4.0 cc) is diluted 1:1 with quartz chips as inert diluent and is then loaded into a 0.5 inch OD SS tube. Feed compositions range from 25-30% ethane, 8-11% $O_2$, and 20-33% steam. Gas and liquid products are analyzed by gas chromatography. The results of Examples 1-6 are given in Table 1, where HAc represents acetic acid. All percentages in Table 1 are calculated on a molar basis.

TABLE 1

|  | Temp (° C.) | Pres. (psig) | GHSV (hr$^{-1}$) | C$_2$H$_6$ in feed (%) | O$_2$ in feed (%) | H$_2$O in feed (%) | C$_2$H$_6$ conv. (%) | C$_2$H$_4$ sel. (%) | HAc sel. (%) | C$_2$H$_4$ yield (%) | HAc yield (%) | C$_2$H$_4$:HAc ratio |
| --- | --- | --- | --- | --- | --- | --- | --- | --- | --- | --- | --- | --- |
| Ex 1 | 330 | 0 | 3000 | 30.0 | 10.5 | 20.0 | 12.4 | 96.0 | 4.0 | 11.3 | 0.5 | 24.0 |
| Ex 2 | 300 | 100 | 3600 | 25.0 | 8.7 | 33.4 | 17.2 | 76.7 | 22.5 | 12.1 | 3.6 | 3.4 |
| Ex 3 | 270 | 200 | 4275 | 30.7 | 10.1 | 21.1 | 12.6 | 65.8 | 33.8 | 8.1 | 4.2 | 1.9 |
| Ex 4 | 360 | 0 | 3000 | 30.0 | 10.5 | 20.0 | 30.6 | 96.7 | 2.4 | 28.3 | 0.7 | 40.2 |
| Ex 5 | 330 | 100 | 3600 | 25.0 | 8.7 | 33.4 | 39.6 | 83.9 | 11.4 | 26.9 | 3.7 | 7.4 |
| Ex 6 | 275 | 200 | 4275 | 30.7 | 10.1 | 21.1 | 36.4 | 77.4 | 16.9 | 27.0 | 5.9 | 4.6 |

The Mo/V/Te/Nb catalyst shows surprisingly high ethylene selectivity when run at typical atmospheric pressure conditions. Examples 1 and 4 show those results: ethylene selectivities are greater than 96%.

The data in Table 1 also show the effect of increasing pressure (and thus lowering temperature) on ethylene/HAc ratio. Examples 1-3 and Examples 4-6 show a clear effect of pressure on lowering the ethylene/HAc product ratio.

Finally, the lowest ethylene/HAc ratios, for a given conversion range, are observed for the Pd-containing catalysts (Examples 3 and 6). A surprisingly low ratio of less than 2 is observed in Example 3.

What is claimed is:

1. A process comprising catalytically converting ethane to ethylene and acetic acid in the presence of oxygen at a temperature of 450° C. or less in the gas phase wherein the catalyst has the empirical formula MoV$_a$Nb$_b$Te$_c$Z$_d$O$_n$ wherein Z is Pd, a =0.01 to less than 1.0, b=0.01 to less than 1.0, c=0.01 to less than 1.0, d=a positive number less than 1.0 and n is determined by the oxidation states of the other elements.

2. The process of claim 1 wherein the converting is conducted at a pressure of from 1 to 30 atmospheres absolute.

3. The process of claim 1 wherein the converting is conducted at a temperature of from 150° C. to 450° C.

4. The process of claim 1 wherein at least part of the product of the process is employed in the production of vinyl acetate.

5. The process of claim 1 wherein the ratio of ethylene to acetic acid is less than 2.

6. The process of claim 1 wherein unreacted ethane is purified and recycled.

7. The process of claim 1 wherein the product acetic acid is condensed.

8. The process of claim 1 wherein the converting is conducted in a reactor system comprising one or more fixed and/or fluidized bed reactors.

9. The process of claim 8 wherein the system comprises more than one reactor and one of the reactors is in catalyst regeneration mode.

10. The process of claim 1 wherein the catalyst consists essentially of the catalyst of the empirical formula.

* * * * *